(12) United States Patent
Guery et al.

(10) Patent No.: US 9,161,889 B2
(45) Date of Patent: Oct. 20, 2015

(54) NON-AQUEOUS ORAL CARE COMPOSITION

(71) Applicant: Conopco, Inc., Englewood Cliffs, NJ (US)

(72) Inventors: Julie Savine Camille Guery, Singapore (SG); Edward George Pelan, Rotterdam (NL); Lin Wang, Shanghai (CN); Weizheng Zhou, Shanghai (CN)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

(21) Appl. No.: 14/388,837

(22) PCT Filed: Mar. 20, 2013

(86) PCT No.: PCT/EP2013/055763
§ 371 (c)(1),
(2) Date: Sep. 29, 2014

(87) PCT Pub. No.: WO2013/149830
PCT Pub. Date: Oct. 10, 2013

(65) Prior Publication Data
US 2015/0086493 A1   Mar. 26, 2015

(30) Foreign Application Priority Data

Apr. 5, 2012   (WO) ................ PCT/CN2012/000434

(51) Int. Cl.
| | |
|---|---|
| *A61K 8/02* | (2006.01) |
| *A61K 8/96* | (2006.01) |
| *A61K 8/34* | (2006.01) |
| *A61K 8/24* | (2006.01) |
| *A61K 8/86* | (2006.01) |
| *A61Q 11/00* | (2006.01) |
| *A61K 8/25* | (2006.01) |
| *A61K 8/26* | (2006.01) |
| *A61K 8/41* | (2006.01) |

(52) U.S. Cl.
CPC ............ *A61K 8/0204* (2013.01); *A61K 8/24* (2013.01); *A61K 8/25* (2013.01); *A61K 8/26* (2013.01); *A61K 8/345* (2013.01); *A61K 8/416* (2013.01); *A61K 8/86* (2013.01); *A61K 8/965* (2013.01); *A61Q 11/00* (2013.01); *A61K 2800/31* (2013.01)

(58) Field of Classification Search
USPC .............................................. 424/49, 52, 402
See application file for complete search history.

(56) References Cited

U.S. PATENT DOCUMENTS

| | | |
|---|---|---|
| 5,614,175 A | 3/1997 | Winston |
| 2007/0071703 A1 | 3/2007 | Lin |

FOREIGN PATENT DOCUMENTS

| | | |
|---|---|---|
| GB | 1492660 | 11/1977 |
| GB | 710129 | 11/2012 |
| WO | WO0101940 | 1/2001 |
| WO | WO0172262 | 10/2001 |
| WO | WO2011160996 | 12/2011 |

OTHER PUBLICATIONS

IPRP2 in PCTEP2013055763, Jul. 1, 2013.
Search Report in EP12167714, Nov. 16, 2012.
Search Report in PCTEP2013055763, Jul. 1, 2013.
Written Opinion in EP12167714, Nov. 16, 2012.
Written Opinion in PCTEP2013055763, Jul. 1, 2013.

*Primary Examiner* — Walter Webb
(74) *Attorney, Agent, or Firm* — Greenberg Traurig, LLP

(57) ABSTRACT

Disclosed is a non-aqueous oral care composition comprising an organoclay, carrier humectant and a calcium source. The non-aqueous oral care composition of the present invention is stable, has rheological characteristics of a hydrous oral care composition, and does not require a manufacturing step of heating and cooling.

14 Claims, 3 Drawing Sheets

NON-AQUEOUS ORAL CARE COMPOSITION

TECHNICAL FIELD

The present invention relates to a non-aqueous oral care composition. In particular, the non-aqueous oral care composition comprises organoclay, carrier humectant, and calcium source. The non-aqueous oral care composition is surprisingly stable and may be manufactured by a simple process. Moreover, the present invention relates to a process of preparing the composition of the present invention.

BACKGROUND OF THE INVENTION

Oral care products, such as toothpaste, are usually formulated from an aqueous base containing a structuring agent. Such structuring agent is used to tune the rheological profile of the oral care product to have special characteristics. Thus, such rheological behaviour would bring benefits to the oral care product, for example, easy manufacture process, stable oral care formulation, and easiness of squeezing for consumer use.

However, there are many ingredients used in oral care product which are physically or chemically incompatible with water. One of the solutions to this problem is to provide such ingredient in a non-aqueous oral care product.

US patent with U.S. Pat. No. 5,614,175 (Enamelon Inc.) is said to disclose a stable, single part, non-aqueous product for remineralizing lesions in tooth comprising at least one water-soluble calcium salt, and at least one water-soluble phosphate salt.

We have found that when changing from aqueous base to non-aqueous base, one of the main challenges is how to tune the rheological behaviour of the oral care composition to make it behave rheologically like an aqueous oral care composition. Such rheology would have an important impact on the manufacture, stability and consumer perception of product.

International application with publication number WO 2011/160996 (Unilever) discloses a non-aqueous oral care composition with a liquid continuous phase comprising a thickening agent, a humectant, and one or more liquid polyethylene glycols having a melting point below 25° C., in which the liquid continuous phase is structured with crystals of one or more solid polyethylene glycols having a melting point of 25° C. or above. The invention also provides a process of preparing a non-aqueous oral care composition as defined above, comprising the steps of forming a mixture comprising the thickening agent, the humectant, the liquid polyethylene glycol(s) and the solid polyethylene glycol(s), heating the mixture to a temperature above the melting point of the solid polyethylene glycol(s), and cooling the mixture to form crystals of the solid polyethylene glycol(s).

We have recognized a need to develop a non-aqueous oral care composition which is easy to manufacture, stable and/or has good consumer perception, and the present invention, therefore, is directed to a non-aqueous oral care composition comprising an organoclay, carrier humectant, and a calcium source. It is unexpectedly found that the non-aqueous oral care composition is easy to be manufactured without heating and cooling steps. The composition is surprisingly stable, cost-effective, and has suitable viscosity characteristics in absence of water.

DEFINITIONS

Clay

"Clay", as used herein, means combinations of one or more clay minerals with traces of metal oxides and organic matter, for example, bentonite, China clay, primary kaolin, laponite. "Clay mineral" as used herein, means hydrous aluminium phyllosilicates, sometimes with variable amounts of iron, magnesium, alkali metals, alkaline earths, and other cations, for example, clay mineral of kaolin group, smectite group, chlorite group, pyribole group. "Organoclay", as used herein, means organophilic cation modified clay and/or clay mineral derived from clay and/or clay mineral by replacing at least some of the exchangeable inorganic cations by organic cations to render the surface hydrophobic. "Hydrophilic clay", as used herein, means a naturally-occurred, synthetic or modified clay and/or clay mineral which is attracted to water, and/or tends to hydrate.

Non-Aqueous

"Non-aqueous", as used herein, means less than 1.5%, and preferably less than 1.0%, and more preferably less than 0.75% and even more preferably still less than 0.5% and most preferably from 0.0 to 0.1% of water by weight, based on total weight of the oral care composition, including all ranges subsumed therein. "Aqueous", as used herein, means greater than 1.5%, and preferably greater than 5%, and more preferably greater than 10% and more preferably still greater than 15% and most preferably from 20 to 90% of water by weight, based on total weight of the oral care composition, including all ranges subsumed therein.

Solubility

"Soluble" and "insoluble", as used herein, means the solubility of a source (e.g., like calcium salts) in water at 25° C. and atmospheric pressure. "Soluble" means a source that dissolves in water to give a solution with a concentration of at least 0.1 moles per liter. "Insoluble" means a source that dissolves in water to give a solution with a concentration of less than 0.001 moles per liter. "Slightly soluble", therefore, is defined to mean a source that dissolves in water to give a solution with a concentration of greater than 0.001 moles per liter and less than 0.1 moles per liter.

Particle Size

"Size" of platelet-like particle as used herein means the longest size measurable in any dimension. "Length" of the rod-like particle as used herein means the size of the longest dimension. "Width" of the rod-like particle as used herein means the size of the second longest dimension. The value of the size is reported as a number average particle size if they are expressed in average value. Particle size can be measured, for example by Scanning Electron Microscopy (SEM).

Viscosity

Viscosity of an oral care composition is the value taken at room temperature (25° C.) using an Anton Paar Rheometer MCR501, plate-plate sandblasted geometry with 25 mm diameter and a gap of 1 mm, at a shear stress of 1 Pa.

Miscellaneous

Except in the examples, or where otherwise explicitly indicated, all numbers in this description indicating amounts of material or conditions of reaction, physical properties of materials and/or use may optionally be understood as modified by the word "about".

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In the first aspect, the present invention is directed to a non-aqueous oral care composition comprising:
(a) organoclay;
(b) carrier humectant; and
(c) calcium source.

In the second aspect, the present invention is directed to a process of preparing a non-aqueous oral care composition of the present invention comprising the steps of forming a mixture comprising organoclay, carrier humectant, and calcium source at a temperature below 50° C.

All other aspects of the present invention will more readily become apparent upon considering the detailed description and examples which follow.

DETAILED DESCRIPTION

Figure 1:
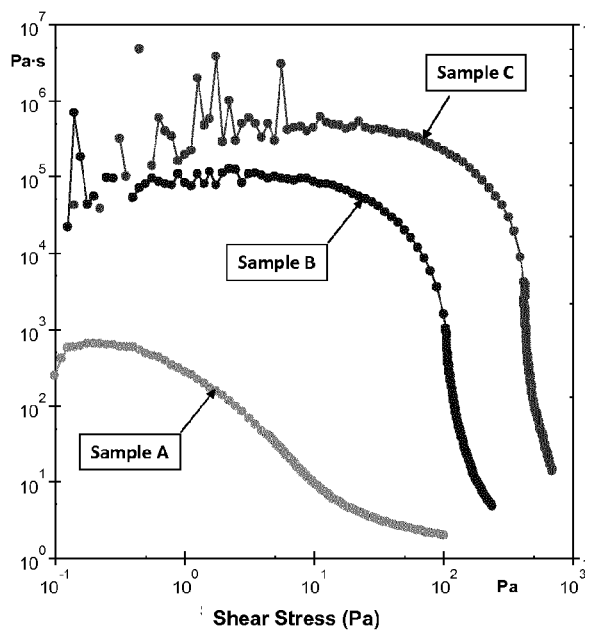
FIG. 1 is the rheological profiles of simplified non-aqueous compositions comprising Garamite 1210 with different concentrations.

The organoclay of the present invention comprises the product of reaction by utilizing a clay mineral. The clay mineral is preferably either natural or synthetic, either planar hydrous phyllosilicates or non-planar hydrous phyllosilicates. Preferably the clay mineral comprises mineral of smectite group, pyribole group, kaolin group or a mixture thereof.

More preferably the clay mineral comprises mineral of smectite smectite group, pyribole group or a mixture thereof. Even more preferably, the clay mineral comprises montmorillonite, palygorskite or a mixture thereof. Still even more preferably, the clay mineral comprises palygorskite. Most preferably, the clay mineral comprises montmorillonite and palygorskite. Prior to use in producing organoclay, the clay mineral is preferably converted to sodium form if the clay is not in this form. Both processed and/or unprocessed clay mineral can be used to produce the organoclay, preferably processed clay mineral is used.

In certain embodiments, the clay mineral preferably comprises montmorillonite in amount of no greater than 90%, more preferably no greater than 80% by weight of the clay mineral. It is preferred that the amount of montmorillonite is at least 5% by weight of the total clay mineral, more preferably at least 15% by weight of the total clay mineral.

Preferably, the organoclay comprises the product of reaction by a clay mineral with an organic salt which can exchange organophilic cations with clay. Such organic salt comprises at least one hydrocarbon radical which can render the surface of the cation-exchanged clay mineral hydrophobic. Preferably the organic salt comprises quaternary ammonium salt, quaternary phosphonium salt, sulfonium salt, or a mixture thereof. More preferably, the organic salt is quaternary ammonium salt. Even more preferably, the organic salt has a formula:

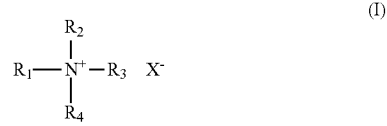

(I)

Wherein the $R_1$ is alkyl or alkenyl group having 8 to 24 carbon atoms, $R_2$, $R_3$, and $R_4$ are independently selected from group of alkyl or alkenyl group having from 1 to 24 carbon atoms or aralkyl group having from 7 to 12 carbon atoms, and X is selected from Cl, Br, I, OH, $CH_3SO_4$, or $CH_3COO$. Most preferably, the organic salt is stearyldimethylbenzylamonium chloride or has a formula of $RR'(CH_3)_2N^+Cl^-$, wherein R and R' are independently C14 to C20 alkyl group.

Preferably, the organoclay suitable for the present invention has a platelet-like shape or rod-like shape. More preferably, the organoclay is rod-like. When the organoclay is platelet-like, the preferred size is from 100 nm to 50 microns. More preferred size is from 500 nm to 20 microns. Even more preferred size is from 2 to 10 microns. When the organoclay is rod-like, the preferred length is from 200 nm to 50 microns. More preferred length is from 500 nm to 20 microns. Even more preferred length is from 1 micron to 5 microns. The preferred width is from 1 nm to 2 microns, more preferred from 10 nm to 500 nm, even more preferred from 30 nm to 300 nm. Without being limited to any theory or explanation, the present inventors believe that smaller organoclay has high specific surface area and therefore has better structuring function.

The preferred concentration depends on the type and size of the organoclay. However, typically the organic clay is present in the oral care composition in amount from 0.1 to 50% by weight of the total composition, more preferably from 0.5 to 15% by weight of the total composition, even more preferably from 1 to 10% by weight of the total composition, and most preferably from 1.5 to 6% by weight of the total composition.

Illustrative examples of organoclay suitable for the present invention include, for example, Tixogel™ MP250, Tixogel™ VZ, Tixogel™ VZV, Tixogel™ LGM, Garamite™ 1210, Garamite™ 1959, Claytone™ 40, Claytone™ HY, Claytone™ HT from Rockwood Specialties, Inc.

Suitable carrier humectant of the present invention comprises, for example, glycerine, sorbitol, propylene glycol, dipropylene glycol, diglycerol, triacetin, mineral oil, polyethylene glycol, alkane diols like butane diol and hexanediol, ethanol, pentylene glycol, xylitol, or a mixture thereof. Preferably, the carrier humectant comprises glycerine, sorbitol, propylene glycol, polyethylene glycol or a mixture thereof. More preferred carrier humectant is glycerine and/or polyethylene glycol-400 (PEG-400) because these two materials are excellent materials when used as humectant in toothpaste formulation. The carrier humectants should, in any case, be substantially free of water, and preferably, non-aqueous.

The carrier humectant is preferably present in the oral care composition in amount from 10 to 90% by weight of the oral care composition. More preferably, the oral care composition comprises from 25 to 80%, even more preferably from 45 to 70% of carrier humectant by weight of the oral care composition.

Typically, the weight ratio of organoclay to carrier humectant is in the range from 1:1000 to 10:1. More preferably, the weight ratio of organoclay to carrier humectant is in the range from 1:300 to 1:1, more preferably from 1:100 to 1:3 and even more preferably from 1:50 to 1:5 and most preferably from 1:35 to 1:7.

The calcium source suitable for use in this invention is limited only to the extent that the calcium source may be used in oral care composition. It could be either water soluble or insoluble. In a preferred embodiment, the calcium source employed is insoluble or slightly soluble in water, but most preferably, insoluble in water.

Non-limiting example of water soluble calcium salts suitable for the present invention include, for example, calcium chloride, calcium nitrate, calcium acetate.

Illustrative examples of the types of calcium source that may be used in this invention include, for example, calcium phosphate, calcium gluconate, calcium oxide, calcium lactate, calcium carbonate, calcium hydroxide, calcium sulfate, calcium carboxymethyl cellulose, calcium alginate, calcium salts of citric acid, calcium silicate, mixtures thereof or the like. In a preferred embodiment the calcium source comprises calcium carbonate, calcium silicate, bioactive glass or a combination thereof. More preferably, the calcium source comprises calcium silicate, bioactive glass or a combination thereof.

When a calcium silicate composite material is employed, the ratio of calcium to silicon (Ca:Si) may be from 1:10 to 3:1. The Ca:Si ratio is preferably from 1:5 to 2:1, and more preferably, from 1:3 to 2:1, and most preferably, from about 1:2 to 2:1. The calcium silicate may comprise mono-calcium silicate, bi-calcium silicate, or tri-calcium silicate whereby ratios of calcium to silicon (Ca:Si) should be understood to be atom ratios.

Bioactive glass which may be used as the calcium source in the present invention comprises calcium and optionally phosphate ions. Suitable bioactive glasses are described, for example in WO 2010/041073 (BIOFILM LTD), WO 2009158564 (NOVAMIN TECHNOLOGY INC), WO 99/13852 (UNIV MARYLAND), WO 2005/063185 (NOVAMIN TECHNOLOGY INC), WO 96/10985 (BIOXID OY) and/or WO 97/27148 (UNIV MARYLAND) all of which International patent applications are hereby incorporated by reference in their entirety.

The oral care composition of the present invention comprises the calcium source typically in amount from 0.1 to 60% by weight of the oral care composition. More preferably, the calcium source is present in the oral care composition in amount from 0.5 to 50%, still more preferably, from 1 to 40%, and even more preferably from 2 to 30% by weight of the oral care composition. In the most preferred embodiment, the calcium source is present in the oral care composition in amount from 5 to 20% by weight based on total weight of the oral care composition and including all ranges subsumed therein.

The weight ratio of the organoclay to the calcium source is preferably in the range of from 1:1.2 to 1:20, more preferably from 1:2 to 1:20, even more preferably from 1:4 to 1:10.

In an embodiment of the present invention, the oral care composition may further comprise phosphate source for in-situ generation of calcium phosphate on teeth. Illustrative examples of the types of phosphate source suitable for use in this invention include monosodium phosphate, sodium dihydrogen phosphate, disodium hydrogen phosphate, sodium pyrophosphate, tetrasodium pyrophosphate, sodium tripolyphosphate, sodium hexametaphosphate, potassium di hydrogenphosphate, trisodium phosphate, tripotassium phosphate, mixtures thereof or the like. The phosphate source is preferably water soluble.

Typically, the phosphate source makes up from 0.5 to 15%, and preferably, from 2 to 12%, and most preferably, from 4 to 9% by weight of the oral care composition, based on total weight of the oral care composition and including all ranges subsumed therein.

Being non-aqueous, the composition of the invention is particularly suitable as a vehicle for oral care actives which may be physically or chemically incompatible with water, or which may function less efficiently in an aqueous environment. Specific examples of oral care actives which may be included in the compositions of the invention include: fluoride sources such as sodium fluoride, stannous fluoride, sodium monofluorophosphate, potassium fluoride, zinc ammonium fluoride, tin ammonium fluoride, calcium fluoride, cobalt ammonium fluoride and mixtures thereof; plant-derivable antioxidants such as flavonoid, catechin, polyphenol, and tannin compounds and mixtures thereof; antioxidant vitamins such as tocopherols and/or derivatives thereof, ascorbic acid and/or derivatives thereof and mixtures thereof; enzymes such as lysozyme, mutanase, protease, amylase, dextranase and mixtures thereof.

The oral care composition of the present invention may further comprise ingredients which are common in the art.

Preferably the composition comprises at least 0.01% surfactant by weight of the composition, more preferably at least 0.1% and most preferably from 0.5 to 7%. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used. More preferably the surfactant comprises or is anionic surfactant. The preferred anionic surfactants are sodium lauryl sulphate and/or sodium dodecylbenzene sulfonate. Most preferably the surfactant is sodium lauryl sulphate.

Preferably the oral care composition will comprise an abrasive cleaning agent in an amount of from 3 to 75% by weight based on the total weight of the dentifrice. Suitable abrasive cleaning agents include particulate abrasive materials such as abrasive silicas, aluminas, calcium carbonates, zirconium silicate, polymethylmethacrylate, dicalcium phosphates, calcium pyrophosphates, hydroxyapatites, tri metaphosphates, insoluble hexametaphosphates and agglomerates and/or mixtures thereof.

The oral care composition described herein may comprise optional ingredients which are common in the art. These ingredients include antimicrobial agents, anti-inflammatory agents, anti-caries agents, plaque buffers, vitamins, plant extracts, desensitizing agents, anti-calculus agents, biomolecules, flavors, proteinaceous materials, preservatives, opacifying agents (especially titanium dioxide), coloring agents, pH-adjusting agents, sweetening agents, particulate abrasive materials, polymeric compounds, buffers and salts to buffer the pH and ionic strength of the compositions, and mixtures thereof.

Such ingredients typically and collectively make-up less than 20% by weight of the oral care composition described herein, and preferably, from 0.0 to 15% by weight, and most preferably, from 0.01 to 12% by weight of the composition, including all ranges subsumed therein.

The composition may be manufactured in any suitable manner. However, preferably, the process of preparing the composition of the present invention comprises the step of forming a mixture comprising organoclay, carrier humectant, and calcium source at temperature below 50° C., more preferably from 0 to 40° C., even more preferably from 10 to 30° C. Preferably, the step of forming a mixture is conducted by a high pressure homogenizer and/or a high speed stirrer.

Preferably the mixture is packaged after formation. In a particularly preferred embodiment the temperature of the mixture does not exceed 50° C. for more than 1 minute between the step of the forming and packaging the mixture. Most preferably the temperature does not exceed 50° C. for more than 10 seconds. Even more preferably the temperature does not exceed 50° C. for more than 1 second.

Preferably, the composition is toothpaste or gel. In toothpaste or gel form, the composition may be packaged in a conventional plastic laminate, metal tube or a single compartment dispenser. The same may be applied to dental surfaces by any physical means, such as a toothbrush, fingertip or by an applicator directly to the sensitive area.

When the oral care composition of this invention is a toothpaste or gel, the same typically has a viscosity from about 200 to 200,000 Pascal second, more preferably from 500 to 50,000 Pascal second, even more preferably from 800 to 35,000 Pascal second, and most preferably, from 1,200 to 20,000 Pascal second.

The oral care composition of this invention can be used in a method of making improvements in the mouth of an individual comprising the step of contacting teeth of an individual with the oral care composition. Preferably, the improvement include providing at least one benefit selected from improved oral hygiene, improved tooth whitening, improved tooth mineralization, or combination thereof.

The composition can be effective even when used in an individual's daily oral hygiene routine. For example, the composition may be brushed onto the teeth and/or be rinsed around the inside of the mouth of the individual. The composition may, for example, be contacted with the teeth for a time period of one second to 20 hours. More preferably from 10 s to 10 hours, more preferably still from 30 s to 1 hour and most preferably from 1 minute to 5 minutes. The composition may be used daily, for example for use by an individual once, twice or three times per day.

EXAMPLES

Clay Materials

Garamite 1210 comprises mainly alkyl quaternary ammonium clay. By Scanning Electron Microscopy, it was found that Garamite 1210 contains rod-like clay mineral with length from 1 to 3 μm and width from 50 to 200 nm and platelet-like clay mineral with size from 2 to 20 μm. According to the surface morphology, it is inferred that Garamite 1210 is more likely prepared by material comprising palygorskite and montmorillonite.

Garamite 1958 comprises mainly alkyl quaternary ammonium clay and has similar surface morphology with Garamite 1210. Therefore it is inferred that Garamite 1958 is also prepared from material comprising palygorskite and montmorillonite.

Tixogel MP250 comprises benzyl(hydrogenated tallow alkyl)dimethyl bentonite (CAS number: 71011-24-0) in amount from 95 to 99 wt %. It is platelet-like with size from 2 to 20 μm. Bentonite is clay comprising mostly montmorillonite.

Tixogel VPV comprises di-($C_{14}$-$C_{18}$-alkyl)dimethyl ammonium bentonite (CAS number: 226226-22-8) in amount from 95 to 99 wt %. It is platelet-like with size from 2 to 20 μm.

Veegum Gtanules, Veegum Ultra Gtanules, Gelwite H, Optigel CK, and Laponite XLG are all hydrophilic clays.

All these clay materials were acquired from Rockwood Specialties, Inc.

Rheological Profile of Toothpaste

The typical rheological profile for aqueous toothpaste comprises following distinct characteristics.

Zero-shear rate viscosity is obtained at the low-shear-stress region (shear stress less than 50 Pa). In this region, typical toothpaste is almost Newtonian, presenting a relatively low dependence upon shear stress. The zero-shear rate viscosity determines the rate of sedimentation of any solid material and insures the stability of paste during storage.

The yield stress is characterised by the point in the rheological flow curve where the viscosity-stress relationship displays its highest negative gradient. For toothpaste use, this will govern the flow of the paste but also the paste's appearance on the brush. The yield stress has to be low enough to enable paste to flow but high enough to prevent sagging and penetration of the paste in the brush hairs by gravity.

The squeezing shear-rate viscosity is characterised as the viscosity with a shear rate of 20 to 40 $s^{-1}$. This shear-rate is estimated as the range of shear rate used during squeezing the toothpaste out from the tube which relates to the easiness of squeezing toothpaste.

The value of viscosity at high shear stress is related to process. Suitable viscosity at high shear stress would make the manufacture of toothpaste easier.

All these important characteristics are desirable for commercial toothpastes.

Example 1

This example demonstrates the ability of organoclay to structure non-aqueous formulation.

Experimental Section

The simplified non-aqueous formulations were prepared according to the ingredients and concentrations in Table 1. Glycerine and PEG-400 were mixed first, and then the organoclay was added step by step under the stirring with speed of 500 rpm by using stirrer (T18 basic Ultra-turrax, IKA, Germany). Finally, a homogeneous non-aqueous formulation was obtained.

Rheological Test

The rheological measurements were performed using an Anton Paar Rheometer MCR501. Plate-plate sandblasted geometry with 25 mm diameter and a gap of 1 mm was used (PP25/Sand Cap Plate P-TEK150/80-77 in Aluminium sandblasted). Temperature within the sample (25° C.) was controlled with a precision of ±0.1° C. via a thermoelectric Peltier module.

Flow curve was obtained via rotational test. The procedure to obtain this curve was divided in two parts. The first of these parts consisted of a logarithmically spaced, stepped sweep in shear stresses (from 0.1 to 400 Pa) where at each discrete shear stress the shear rate was measured as the gradient of the resulting strain/time curve. Once the measured shear rate had exceeded $0.1\ s^{-1}$, the first step was terminated. The data was collected every 4.8 seconds and 20.0 data points were gathered every order of magnitude of shear stress during the first step. The second step in the experiment was a sweep in shear rate from $0.1\ s^{-1}$ to $50\ s^{-1}$. The resultant rheological profile was presented in the format viscosity versus shear stress. The data was collected every 3 seconds for 4 minutes during the second step.

TABLE 1

| | Composition (% w/w) | | | | | |
| | | | Organoclay | | | |
| Sample | Glycerine | PEG-400 | Garamite 1210 | Garamite 1958 | Tixogel MP250 | Tixogel VPV |
|---|---|---|---|---|---|---|
| A | 81.5 | 16.5 | 2.0 | — | — | — |
| B | 79.0 | 16.0 | 5.0 | — | — | — |
| C | 76.5 | 15.5 | 8.0 | — | — | — |
| D | 81.5 | 16.5 | — | 2.0 | — | — |
| E | 81.5 | 16.5 | — | — | 2.0 | — |
| F | 79.0 | 16.0 | — | — | 5.0 | — |
| G | 76.5 | 15.5 | — | — | 8.0 | — |
| H | 81.5 | 16.5 | — | — | — | 2.0 |
| I | 79.0 | 16.0 | — | — | — | 5.0 |
| J | 76.5 | 15.5 | — | — | — | 8.0 |
| K | 74.9 | 15.1 | — | — | — | 10.0 |

Results

Figure 2:
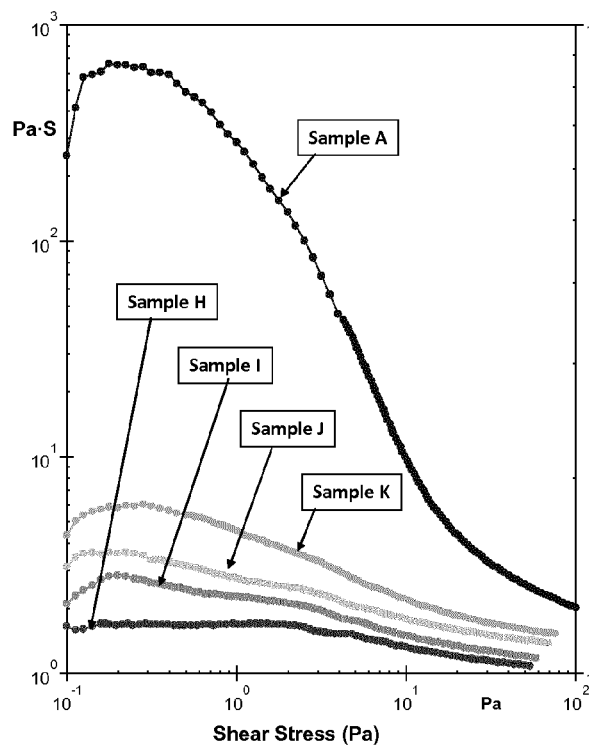
FIG. 2 is the rheological profiles of simplified non-aqueous compositions comprising Tixogel VPV with different concentrations and simplified non-aqueous composition comprising 2 wt % of Garamite 1210 as a benchmark.

The rheological tests of those simplified non-aqueous formulations were conducted. FIG. 1 shows the rheological profiles of sample A, B and C. It is demonstrated that the organoclay, Gramite 1210, has excellent structuring ability even using concentration as low as 2 wt %. These rheological profiles have a zero shear rate relatively high viscosity plateau, a shear-thinning behaviour, and a relatively low viscosity at high shear stress. All these rheological characteristics show the feasibility to be formulated to an oral care formulation. Garamite 1958 is able to lead to similar rheological behaviour of the simplified non-aqueous formulation as Garamite 1210. Sample A and D have almost the same rheological profile (not shown). From the rheological profile of sample E, F, and G (not shown), it is found that Tixogel MP250 also has good structuring ability although it is not as good as Garamite 1210. FIG. 2 shows the rheological profiles of sample H, I, J, and K together with sample A as a benchmark. It is manifested that Tixogel VPV has some structuring ability even using a concentration of 2 wt %, but is less effective than Garamite 1210. It is potential to use Tixogel VPV to tune the rheological profile of non-aqueous oral care composition.

Example 2

This example demonstrates the hydrophilic clay is not as good as organoclay for structuring non-aqueous formulation.
Experimental Section The simplified non-aqueous formulations as listed in Table 2 were prepared by following the similar procedure as described in Example 1. The rheological tests were conducted by following the similar procedure as described in Example 1.

TABLE 2

| | Composition (% w/w) | | | | | | |
| | | | Hydrophilic Clay | | | | |
| Sample | Glycerine | PEG-400 | Veegum Granules | Veegum Ultra Granules | Gelwite H | Optigel CK | Laponite XLG |
|---|---|---|---|---|---|---|---|
| L | 79.0 | 16.0 | 5.0 | — | — | — | — |
| M | 74.9 | 15.1 | 10.0 | — | — | — | — |
| N | 74.9 | 15.1 | — | 10.0 | — | — | — |
| O | 74.9 | 15.1 | — | — | 10.0 | — | — |
| P | 74.9 | 15.1 | — | — | — | 10.0 | — |
| Q | 81.5 | 16.5 | — | — | — | — | 2.0 |
| R | 79.0 | 16.0 | — | — | — | — | 5.0 |
| S | 76.5 | 15.5 | — | — | — | — | 8.0 |
| T | 74.9 | 15.1 | — | — | — | — | 10.0 |

Results

Figure 3:
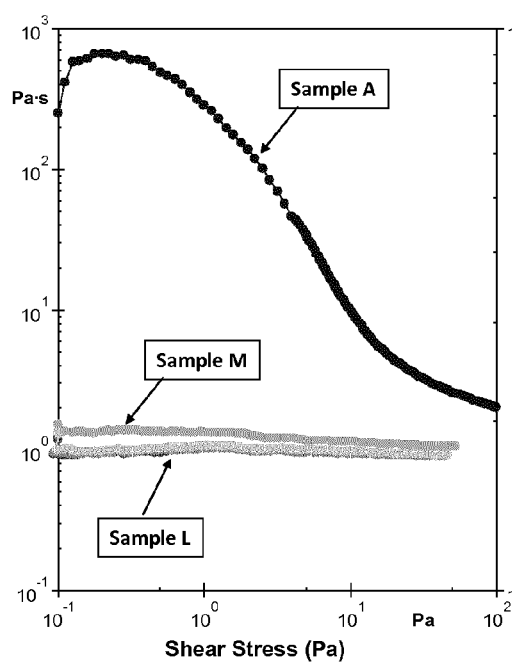
FIG. 3 is the rheological profiles of simplified non-aqueous compositions comprising Veegum Gtanules with different concentrations and simplified non-aqueous composition comprising 2 wt % of Garamite 1210 as a benchmark.
Figure 4:
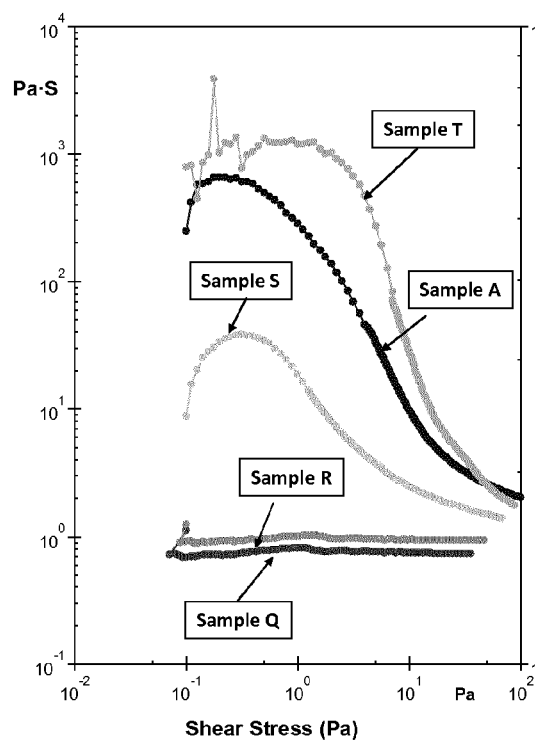
FIG. 4 is the rheological profiles of simplified non-aqueous compositions comprising Laponite XLG with different concentrations and simplified non-aqueous composition comprising 2 wt % of Garamite 1210 as a benchmark.

FIG. 3 shows rheological profiles of sample L, M and A as a benchmark. As can be seen from the flow curve, the viscosity of both sample L and M is quite low, and did not change with shear stress. Veegum Gtanules does not show any structuring ability for such simplified non-aqueous formulation. The rheological profiles of sample N, O, and P (not shown) are similar with that of sample L and M, demonstrating that none of Veegum Ultra Gtanules, Gelwite H, and Optigel CK has the ability for structuring the non-aqueous formulation. FIG. 4 shows the rheological profiles of sample H, I, J, and K together with sample A as a benchmark. The rheological profile of sample Q and R are similar with that other hydrophilic clay. Sample S and T have similar rheological characteristics with that of sample A. It is indicated that only Laponite XLG with a concentration of 8 wt % or more is possible to structure the non-aqueous formulation. If Laponite XLG is present in the formulation with a concentration of 5 wt % or less, it can not serve as structuring agent.

Example 3

This example demonstrates the manufacture process, rheological profile and thermal stability of non-aqueous oral care compositions of the present invention.

Experimental Section

Preparation of Non-Aqueous Toothpaste

The non-aqueous oral care compositions as shown in Table 3 were prepared by following the steps of:
(1) dispersion of organoclay into the non-aqueous solvent mixture under stirring of 8000 rpm in 10 min by a high pressure homogenizer (T18 basic Ultra-turrax, IKA, Germany);
(2) dispersion of SMFP, Sodium saccharin, TSP, and MSP together under stirring of 600 rpm in 10 min by a stirrer (Eurostar power control stirrer, IKA, Germany);
(3) dispersion of CS into the mixture under a stirring of 600 rpm in 15 min;
(4) dispersion of abrasive silica under a stirring of 600 rpm in 15 min;
(5) dispersion of SLS under a stirring of 400 rpm in 5 min;
(6) dispersion of flavour under a stirring of 400 rpm in 5 min; and
(7) dispersion of Timrion under a stirring of 400 rpm in 5 min.

There is no heating or cooling step required for the preparation of such non-aqueous oral care composition of the present invention.

TABLE 3

| Component | Non-aqueous oral care composition | | | |
|---|---|---|---|---|
| (% w/w) | U | V | W | X |
| Glycerine | To 100 | To 100 | To 100 | To 100 |
| PEG-400 | 10.83 | 10.83 | 10.33 | 9.83 |
| Garamite 1210 | 2.00 | — | — | — |
| Garamite 1958 | — | 2.00 | — | — |
| Tixogel MP250 | — | — | 5.00 | — |
| Tixogel VPV | — | — | — | 8.00 |
| Sodium saccharin | 0.20 | 0.20 | 0.20 | 0.20 |
| Sodium monofluorophosphate (SMFP) | 1.11 | 1.11 | 1.11 | 1.11 |
| Timrion MP149 | 0.50 | 0.50 | 0.50 | 0.50 |
| Monosodium Phosphate (MSP) | 3.20 | 3.20 | 3.20 | 3.20 |
| Trisodium Phosphate (TSP) | 3.80 | 3.80 | 3.80 | 3.80 |
| Calcium silicate (CS) | 15.00 | 15.00 | 15.00 | 15.00 |
| Abrasive silica | 6.50 | 6.50 | 6.50 | 6.50 |
| Flavour | 1.20 | 1.20 | 1.20 | 1.20 |
| Sodium Lauryl Sulphate (SLS) | 2.00 | 2.00 | 2.00 | 2.00 |

The rheological profiles of the non-aqueous toothpastes, a commercial aqueous toothpaste, and a commercial non-aqueous toothpaste were then tested by following the similar procedure as described in Example 1. The zero shear-rate viscosity was taken at sheer stress of 1 Pa.

The toothpaste A was stored at 6° C., 20° C. and 45° C. for three month to test the product stability. During the storage time, the toothpaste was squeezed out to check the appearance and stability by naked eye.

TABLE 4

| | Non-aqueous oral care composition | | | | Commercial aqueous toothpaste | Commercial non-aqueous toothpaste |
|---|---|---|---|---|---|---|
| | U | V | W | X | | |
| Viscosity (Pa · s) | 18,374 | 10,487 | 2,350 | 1,911 | 5,230 | 3,720 |

Results

Figure 5:
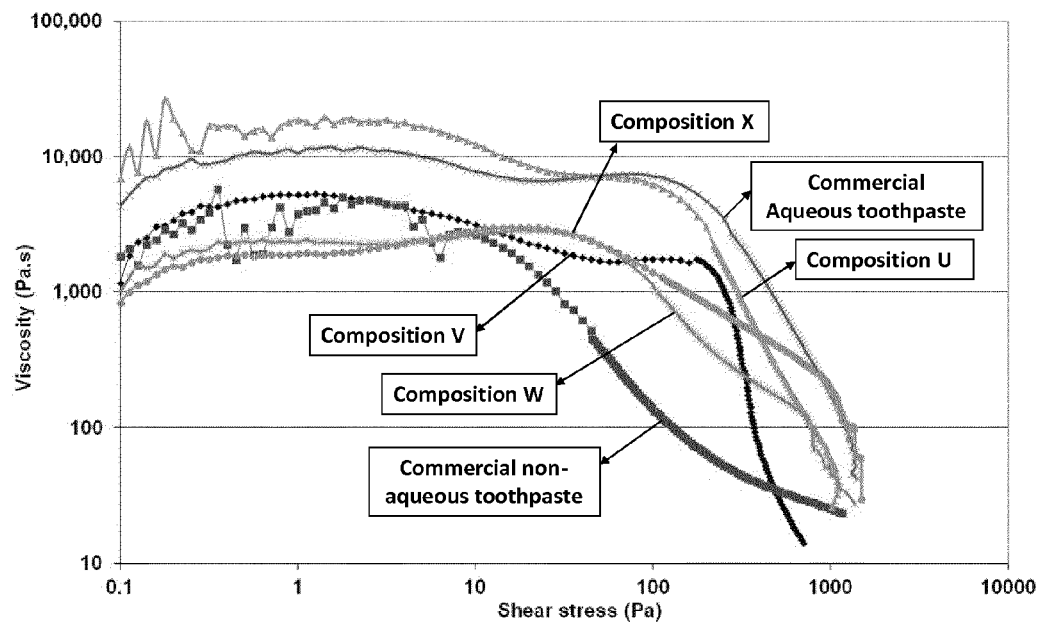
FIG. 5 is the rheological profiles of non-aqueous oral care compositions of the present invention, a commercial non-aqueous toothpaste, and a commercial aqueous toothpaste.

The rheological profiles of the tested toothpaste are plotted in FIG. 5. As can be seen from the figure, all the non-aqueous toothpastes of the present invention have similar rheological profile with that of commercial hydrous toothpaste. The value of each characteristic is suitable for oral care composition. For example, these rheological profiles of the non-aqueous oral care compositions have a zero shear rate relatively high viscosity plateau, a shear-thinning behaviour, and a relatively low viscosity at high shear stress. It is manifested that the non-aqueous toothpaste of the present invention would behave rheologically like the commercial aqueous toothpaste.

Table 4 shows the zero shear-rate viscosities of the non-aqueous oral care compositions of the present invention, the commercial aqueous and non-aqueous toothpastes. The viscosities of the compositions are comparable with the commercial toothpastes, showing good stability of the composition The stability of composition U was also proved to be excellent from the experiment of stability test. The toothpaste was squeezed out after it was stored at 20° C. for one month, two months, and three months respectively. Before usage, the non-aqueous toothpaste was suitable to be squeezed out. After squeezing out on tissue, the shape of the non-aqueous toothpaste strip remained, and the non-aqueous toothpaste was still very homogeneously dispersed, indicating the toothpaste has a suitable zero shearing force viscosity to maintain the stability of non-aqueous toothpaste for long time and different temperature. Similar results were surprisingly obtained also at 6° C. and 45° C. Therefore, the non-aqueous oral care composition is quite stable.

Example 4

This example demonstrates the formation of hydroxy apatite layer by non-aqueous oral care composition.

Experimental Section

Non-aqueous oral care composition U was prepared according to the method in Example 3. Composition U was used to treat the teeth. The teeth (bovine enamel blocks) were hand brushed with diluted toothpaste (toothpaste:water, 3 g:6 g) for 1 min and incubated in toothpaste-water slurry for 1 min after brushing. During the following rinse off stage, each sample was rinsed with deionised water two times (15 ml each rinse). Brushing was performed 3 times per day for four weeks and between brushes samples were stored in simplified simulated body fluid.

After four weeks of brushing, the treated teeth were embedded in epoxy resin, and then cut into thin slices (or cross-sections) with a diamond saw. The slices were subsequently polished with an alumina slurry. In order to observe the boundary of tooth enamel and new in situ formed hydroxyapatite, the slices were incubated in 0.1% citric acid solution for 8 minutes to expose the microstructure of the enamel in the teeth. After washing with water and drying at 50° C. for 24 hours, the cross-sections were observed under Scanning Electronic Microscopy (SEM) to assess how much of new enamel or hydroxyapatite layer had formed.

Results

Figure 6:
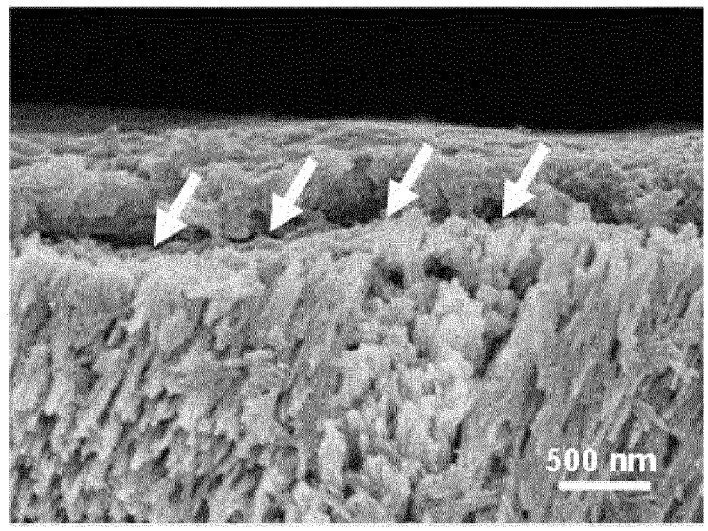
FIG. 6 is the SEM image of a cross-section of an enamel block after brushing for four weeks with a non-aqueous oral care composition according to an embodiment of the present invention.

FIG. 6 shows the cross-section image of tooth after erosion with the citric acid. It can be seen that the enamel of tooth is mainly composed of nanorod-like crystals that are highly organized into enamel prisms. The boundary between tooth enamel and the new hydroxyapatite is distinct and identified by the arrows in the figure. The thickness of the new hydroxyapatite layer is surprisingly about 600 nm after 4 weeks of treatment with the non-aqueous oral care composition of this invention, indicating the formation of new hydroxyapatite layer.

The invention claimed is:

1. A non-aqueous oral care composition comprising:
   (a) organoclay;
   (b) carrier humectant; and
   (c) calcium source,
wherein the weight ratio of the organoclay to the calcium source is in the range of 1:1.2 to 1:20 and the carrier humectant comprises glycerin, sorbitol, propylene glycol, dipropylene glycol, diglycerol, polyethylene glycol, alkane diols, ethanol, pentylene glycol or a mixture thereof.

2. The composition according to claim 1 wherein the composition comprises from 1 to 10% of organoclay by weight of the total composition.

3. The composition according to claim 1 wherein the organoclay comprises the product of reaction utilizing a clay mineral comprising clay mineral of smectite group, pyribole group or a mixture thereof.

4. The composition according to claim 3 wherein the clay mineral comprises montmorillonite, palygorskite or a mixture thereof.

5. The composition according to claim 1 wherein the organoclay comprises the product of reaction of a clay mineral with a quaternium ammonium salt.

6. The composition according to claim 5 wherein the quaternary ammonium salt is stearyldimethylbenzylamonium chloride or has a formula of $RR'(CH_3)_2N^-Cl^-$, wherein R and R' are independently C14 to C20 alkyl group.

7. The composition according to claim 1 wherein the carrier humectant is glycerine and/or propylene glycol-400.

8. The composition according to claim 1 wherein the carrier humectant is present in the composition in amount from 10% to 90% by weight of the composition.

9. The composition according to claim 1 wherein the calcium source is water insoluble and/or slightly soluble.

10. The composition according to claim 8 wherein the calcium source comprises calcium gluconate, calcium oxide, calcium lactate, calcium carbonate, calcium hydroxide, calcium sulfate, calcium carboxymethyl cellulose, calcium alginate, calcium salts of citric acid, calcium silicate, bioactive glass or a mixture thereof, preferably the the calcium source comprises calcium carbonate, calcium silicate, bioactive glass or a combination thereof, more preferably the calcium source comprises calcium silicate, bioactive glass or a combination thereof.

11. The composition according to claim 1 wherein the calcium source is present in the composition in amount from 0.5 to 50% by weight of the composition.

12. The composition according to claim 1 wherein the composition comprises a phosphate source.

13. The composition according to claim 1 further comprising a phosphate source wherein the phosphate source is monosodium phosphate, sodium dihydrogenphosphate, disodium hydrogenphosphate, sodium pyrophosphate, tetrasodium pyrophosphate, sodium hexametaphosphate, monopotassium phosphate, potassium dihydrogenphosphate, dipotassium hydrogenphosphate, trisodium phosphate, tripotassium phosphate or a mixture thereof.

14. A process of preparing the composition according to any one of the preceding claims comprising the steps of forming a mixture comprising organoclay, carrier humectant, and calcium source at temperature below 50° C., wherein the weight ratio of the organoclay to the calcium source is in the range of 1:1.2 to 1:20 and the carrier humectant comprises glycerin, sorbitol, propylene glycol, dipropylene glycol, diglycerol, polyethylene glycol, alkane diols, ethanol, pentylene glycol or a mixture thereof.

* * * * *